United States Patent
Melker

(10) Patent No.: US 9,668,695 B2
(45) Date of Patent: Jun. 6, 2017

(54) PULSE OXIMETER PROBES AND METHODS FOR USING THE SAME

(71) Applicant: Richard J. Melker, Gainesville, FL (US)

(72) Inventor: Richard J. Melker, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 546 days.

(21) Appl. No.: 14/194,999

(22) Filed: Mar. 3, 2014

(65) Prior Publication Data

US 2014/0243631 A1 Aug. 28, 2014

Related U.S. Application Data

(63) Continuation of application No. 11/573,418, filed on Feb. 8, 2007, now Pat. No. 8,679,028.

(Continued)

(51) Int. Cl.
| | |
|---|---|
| *A61B 5/026* | (2006.01) |
| *A61B 5/0295* | (2006.01) |
| *A61B 5/00* | (2006.01) |

(52) U.S. Cl.
CPC .......... *A61B 5/6819* (2013.01); *A61B 5/0261* (2013.01); *A61B 5/0295* (2013.01); *A61B 5/6816* (2013.01)

(58) Field of Classification Search
CPC ...... A61M 2230/005; A61M 2230/205; A61M 2230/432; A61M 2230/42; A61M 16/0003; A61M 16/0051; A61M 16/0057; A61M 16/06; A61M 16/0666; A61M 16/0672; A61M 16/0683; A61M 16/08; A61M 16/20; A61M 2205/3569; A61M 2210/0618; A61M 2210/0625; A61M 2210/0662; A61M 2230/06; A61M 2230/30; A61B 5/0261; A61B 5/0295; A61B 5/6819; A61B 5/02416; A61B 5/14552; A61B 2560/0276; A61B 2562/247; A61B 5/0205;
(Continued)

(56) References Cited

U.S. PATENT DOCUMENTS

| | | | | |
|---|---|---|---|---|
| 4,830,014 A | * | 5/1989 | Goodman | .......... A61B 5/02427 600/310 |
| H001039 H | * | 4/1992 | Tripp, Jr. | ........... A61B 5/14552 128/201.23 |

(Continued)

FOREIGN PATENT DOCUMENTS

| | | |
|---|---|---|
| WO | 9962399 A1 | 12/1999 |
| WO | 0021438 A1 | 4/2000 |

(Continued)

OTHER PUBLICATIONS

Foreign search report for Application No. 14184033.0-1657, dated Jan. 23, 2015.

(Continued)

*Primary Examiner* — Navin Natnithithadha
(74) *Attorney, Agent, or Firm* — Thomas | Horstemeyer, LLC

(57) ABSTRACT

Provided according to embodiments of the invention are photoplethysmography probes designed for use on a user's nasal alar. Methods of using such photoplethysmography probes are also provided herein.

16 Claims, 11 Drawing Sheets

Related U.S. Application Data

(60) Provisional application No. 60/600,548, filed on Aug. 11, 2004.

(58) Field of Classification Search
CPC ..... A61B 5/02427; A61B 5/036; A61B 5/087; A61B 5/0873; A61B 5/14551; A61B 5/4818; A61B 5/4836; A61B 5/6803; A61B 5/6815; A61B 5/6817; A61B 5/682; A61B 5/6826; A61B 5/6829; A61B 5/7282; A61B 5/6816
See application file for complete search history.

(56) References Cited

U.S. PATENT DOCUMENTS

| | | | |
|---|---|---|---|
| 5,335,659 A | 8/1994 | Pologe | |
| 6,909,912 B2* | 6/2005 | Melker | A61B 5/0873 600/323 |
| 7,024,235 B2* | 4/2006 | Melker | A61B 5/0873 600/340 |
| 7,127,278 B2* | 10/2006 | Melker | A61B 5/0873 600/340 |
| 8,641,635 B2* | 2/2014 | Melker | A61B 5/0261 600/504 |
| 8,679,028 B2* | 3/2014 | Melker | 600/500 |
| 8,755,857 B2* | 6/2014 | Melker | A61B 5/0873 128/204.23 |
| 9,004,071 B2* | 4/2015 | Alexander | A61B 1/00108 128/200.26 |
| 9,198,586 B2* | 12/2015 | Melker | A61B 5/0295 |
| 2003/0163033 A1 | 8/2003 | Dekker | |
| 2003/0163050 A1 | 8/2003 | Dekker | |
| 2003/0163054 A1 | 8/2003 | Dekker | |
| 2003/0236452 A1 | 12/2003 | Melker | |
| 2004/0230108 A1* | 11/2004 | Melker | A61B 5/0873 600/340 |
| 2004/0260161 A1* | 12/2004 | Melker | A61B 5/0873 600/340 |
| 2005/0107709 A1* | 5/2005 | Hampel | A61B 5/411 600/476 |
| 2007/0027375 A1* | 2/2007 | Melker | A61B 5/0873 600/340 |
| 2008/0058621 A1* | 3/2008 | Melker | A61B 5/0816 600/330 |
| 2010/0192952 A1* | 8/2010 | Melker | A61B 5/0261 128/204.23 |
| 2012/0078069 A1* | 3/2012 | Melker | A61B 5/0836 600/340 |
| 2013/0092173 A1* | 4/2013 | Alexander | A61B 1/00108 128/207.18 |
| 2013/0096374 A1* | 4/2013 | Alexander | A61B 17/24 600/102 |
| 2013/0172759 A1* | 7/2013 | Melker | A61M 39/281 600/476 |
| 2013/0276785 A1* | 10/2013 | Melker | G06F 19/3468 128/204.23 |
| 2014/0094670 A1* | 4/2014 | Melker | A61B 5/0873 600/324 |
| 2014/0155704 A1* | 6/2014 | Melker | A61B 5/0873 600/301 |
| 2014/0155713 A1* | 6/2014 | Melker | A61B 5/0873 600/324 |
| 2014/0158132 A1* | 6/2014 | Melker | A61B 5/0873 128/204.23 |
| 2014/0180026 A1* | 6/2014 | Melker | A61B 5/0873 600/301 |
| 2014/0243630 A1* | 8/2014 | Melker | A61B 5/0295 600/324 |

FOREIGN PATENT DOCUMENTS

| | | |
|---|---|---|
| WO | 03051198 A1 | 6/2003 |
| WO | 03071938 A1 | 9/2003 |

OTHER PUBLICATIONS

Foreign search report for Application No. 15198577.7, dated Aug. 18, 2016.

Kamal, et al., Skin Photoplethysmography—A review Computer Methods and Programs in Biomedicine, Amsterdam, NL, vol. 38, No. 4, Apr. 1, 1989.

* cited by examiner

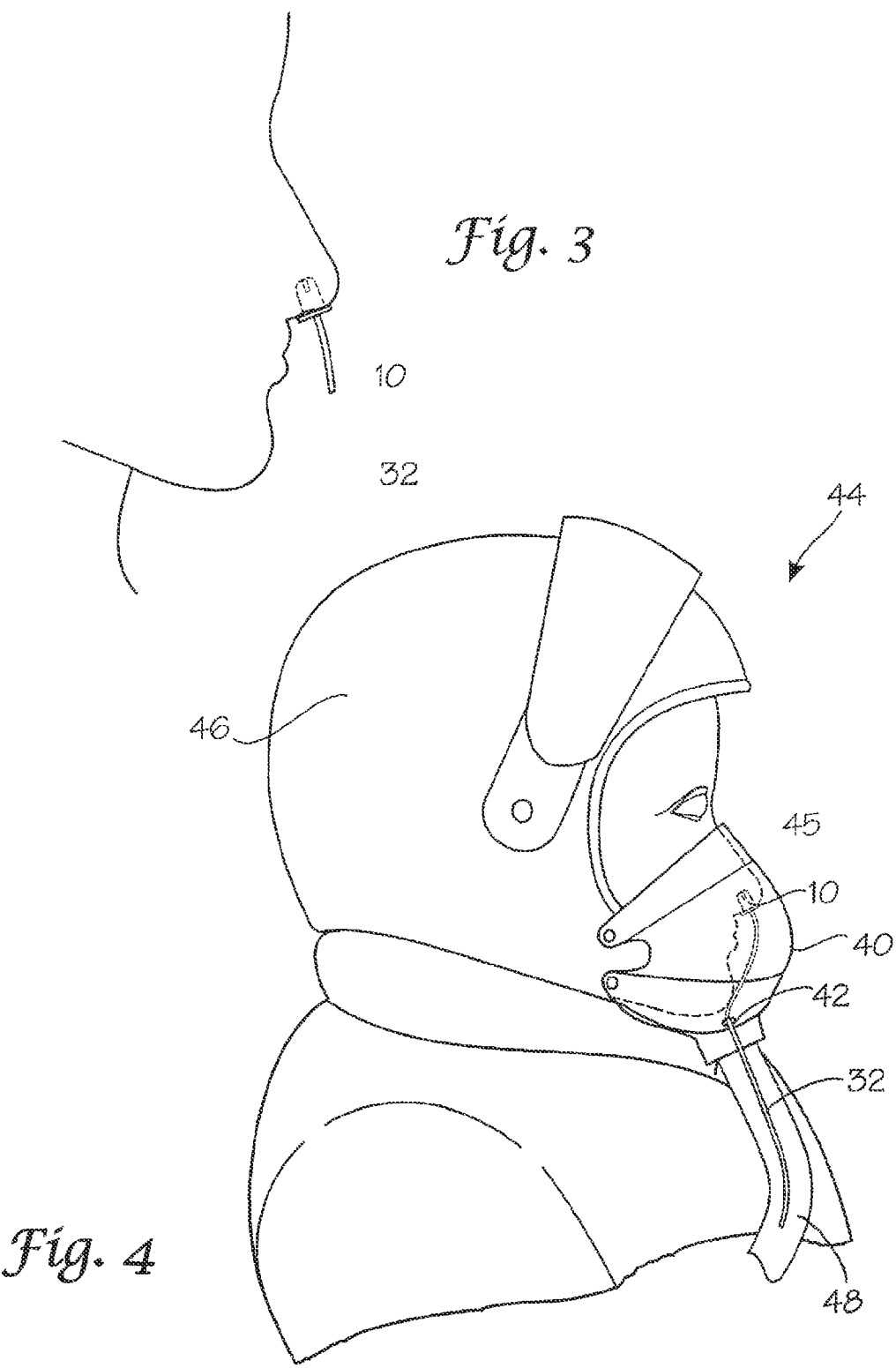

PULSE OXIMETER PROBES AND METHODS FOR USING THE SAME

CROSS-REFERENCE TO RELATED APPLICATIONS

This application is a continuation of U.S. patent application Ser. No. 11/573,418, filed Feb. 8, 2007, which is a national stage of International Patent Application No. PCT/US2005/28355, filed Aug. 10, 2005, which application claims the benefit of U.S. provisional patent Application No. 60/600,548, filed Aug. 11, 2004.

BACKGROUND OF THE INVENTION

Gravity-induced loss of consciousness ("GLOC") is a phenomenon that occurs when someone is subjected to substantially increased gravitational loads (+Gz) for a sustained period. High-performance aircraft, such as fighters, allow maneuvers that generate +Gz that exceed the limits of the human body. This predisposes to GLOC and a serious degrading of physiological and cognitive performance. GLOC is one of the primary physiological threats to pilots and crews of high-performance aircraft. Since the mid 1980s, one branch of the US military, the United States Air Force, has lost 29 aircraft and 22 pilots to GLOC. (*The Effect of Negative Gz Recovery from GLOC on Cerebral Oximetry, Broughton*, presentation at USAF School of Aerospace Medicine, Brooks AFB, Texas (2003).) Similar loss rates can be expected for the other services flying high performance aircraft. In addition to the loss of life, the cost of training and lost aircraft is staggering.

Almost loss of consciousness (ALOC) is even more common than GLOC. Symptoms include euphoria, apathy, displacement, depersonalization, poor response to auditory stimuli, immediate memory difficulties, sensory abnormalities, motor abnormalities, confusion, and dream-like state without loss of consciousness, which are considered precursors of GLOC, which is defined as "A state of altered perception wherein one's awareness of reality is absent as a result of sudden, critical reduction of critical blood circulation caused by increased G forces". (Morrissette K L, McGowan D G. Further support for the concept of a G-LOC syndrome: a survey of military high-performance aviators. Aviat Space Environ Med. 2000; 71:496-500.; Burton R R, G-Induced Loss of Consciousness: Definition, History, Current Status. Aviat Space Environ Med. 1988; 59:2-5.)

Some methods have been developed to increase G-level tolerances, including centrifuge training, weight training, the anti-G suit, positive pressure breathing, anti-G straining maneuvers and postural modification in the cockpit. The current capabilities of trained individuals to maintain clear vision during sustained exposures to +9 Gz, an increase in protected +Gz tolerance of about +4 Gz over World War II fighter pilots, is largely a result of combined use of a G suit and self-protective straining maneuvers such as the M-1, L-1 and pressure breathing, all of which are variants of the Val salva maneuver developed in the 1940s. (*G-induced Loss of Consciousness and its Prevention*, Earl Wood, (1988) Mayo Clinic, Rochester, Minn.) However, despite such training, a review often fatal crashes attributed to GLOC shows that such measures fall short of addressing the problem. Id. The Wood review notes that the likely causes of such failures were: (1) increased capability of jet-powered fighters to sustain, with minimal pilot effort, accelerations in the 7-10 +Gz range for periods longer than the symptom-free 3-8 second cerebral ischemic anoxic period which precedes GLOC, (2) an improperly performed Valsalva-type straining maneuver, and (3) development of a hypotensive vasovagal type reaction.

The inventors believe that currently used techniques do not adequately address the problem of GLOC (which for the purposes of this document pertains to both ALOC and GLOC) because they ultimately put the burden on the pilot to realize when he/she is about to sustain GLOC.

SUMMARY OF THE INVENTION

The subject invention pertains to methods, devices and systems of obtaining plethysmography readings and utilizing plethysomography to identify when pilots are about to experience GLOC and for training pilots to recognize signs and symptoms of impending GLOC. Furthermore, in other embodiments, the invention pertains to methods and devices designed to warn a pilot that he/she is about to sustain GLOC and/or automatically averting catastrophic damage or injuries by directing the plane to take predetermined corrective actions. Finally, the subject invention allows measurements made during training in centrifuges and aircraft to be displayed for real-time feedback to teach the pilot to optimize GLOC prevention maneuvers and to be stored and used to provide an individual pilot's plethysmographic data for developing GLOC "profiles" which can be programmed into flight systems to determine when an individual pilot is entering the early stages of GLOC based on previously collected data.

According to other aspects, the subject invention pertains to novel pulse oximeter probes. The term "pulse oximeter probe" as used herein refers to probes that can be used for pulse oximetry determination of arterial blood oxygen saturation and/or used for plethysmography.

BRIEF DESCRIPTION OF THE DRAWINGS

FIG. 3 shows a side view of a user having a pulse oximeter probe as shown in FIG. 1 inserted and secured in their nose.

FIG. 4 shows a side view of a pilot wearing a mask, having a pulse oximeter probe that interacts therewith.

FIG. 13*a* shows the right and left plethysmograph without depressing the carotid artery. FIG. 13b shows the right and left plethysmograph with pressing the right carotid artery. FIG. 13c shows the right and left plethysmograph after releasing the right carotid artery.

DESCRIPTION OF THE ILLUSTRATED EMBODIMENTS OF THE INVENTION

Figure 1:
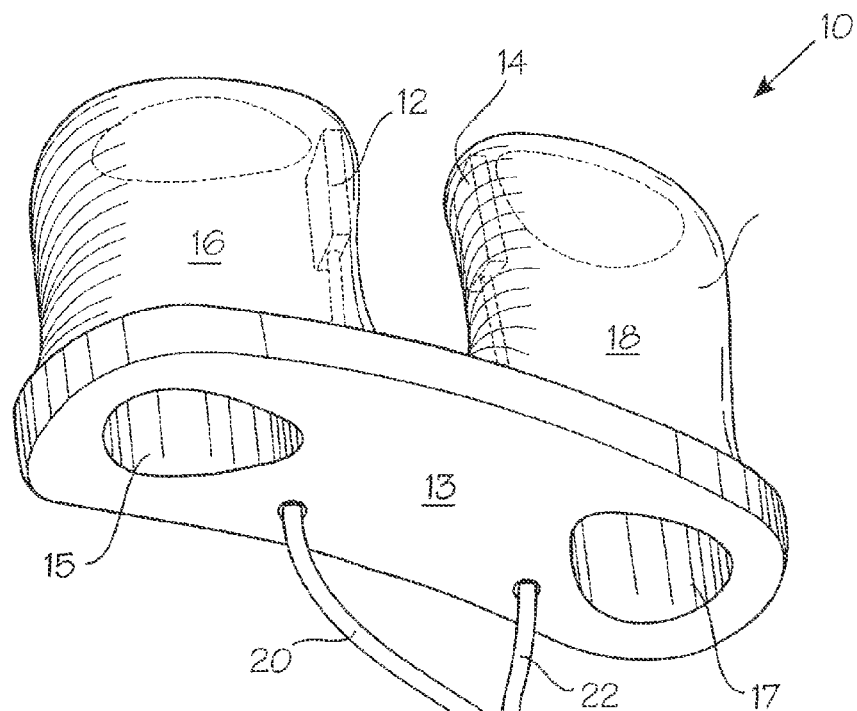
FIG. 1 shows a perspective view of a pulse oximeter/plethysmography probe designed for securement in the nose of the user.

Turning to FIG. 1, a nasal pulse oximeter probe 10 is shown designed for the comfortable placement in the nostrils of a human or non-human. The nasal probe 10 may be made of a wide array of materials, including, but not limited to, silicon, rubber, plastic or other polymer-based materials, or other suitable materials. Preferably, the nasal probe is comprised, at least in part, of materials (similar to hearing aid ear molds) that are soft and flexible as to allow proper comfort by the user, but possess enough rigidity to properly conform to the inner walls of the nose and provide frictional resistance to secure the probe in the user's nose. The nasal probe 10 comprises a first insert 16 having defined therein a channel 15 and a second insert 18 having defined therein a channel 17. Channels 15 and 17 are of a dimension to allow for the free-flowing passage of air as the user inhales and exhales in and out of the user's nose. Positioned in or on the medial wall of insert 16 is a light generating source, such as a light emitting diode (LED). A photodetector 14 is positioned on or in the medial region of insert 18. Wires 20 and 22 are connected to the light generating source 12 in photodetector 14, respectively. To assist in the management of wires 20 and 22, wires 20 and 22 may be secured together by fastener 24, such as a sleeve. Those skilled in the art will appreciate than any means for holding together wires may be used for this purpose, including, but not limited to, a clip, tie, ring, band, etc.

In addition, the inventors do not intend to be limited to the type of probe that may be used. U.S. application Ser. Nos. 10/176,310; 10/751,308; and 10/749,471 disclose various probe embodiments that may be implemented for use in accord with the teachings herein. These applications also teach the functional and technical aspects of the LED and photodetector.

As used herein, the term "central source site" refers to a site above a user's neck, wherein information regarding blood flow at such site correlates with blood flow to the user's brain. Examples of central source sites, include, but are not limited to, the tongue, lip, cheek, nasal nares, nasal septum, nasal alar, pre-auricular region, post-auricular region and ears.

Figure 2:
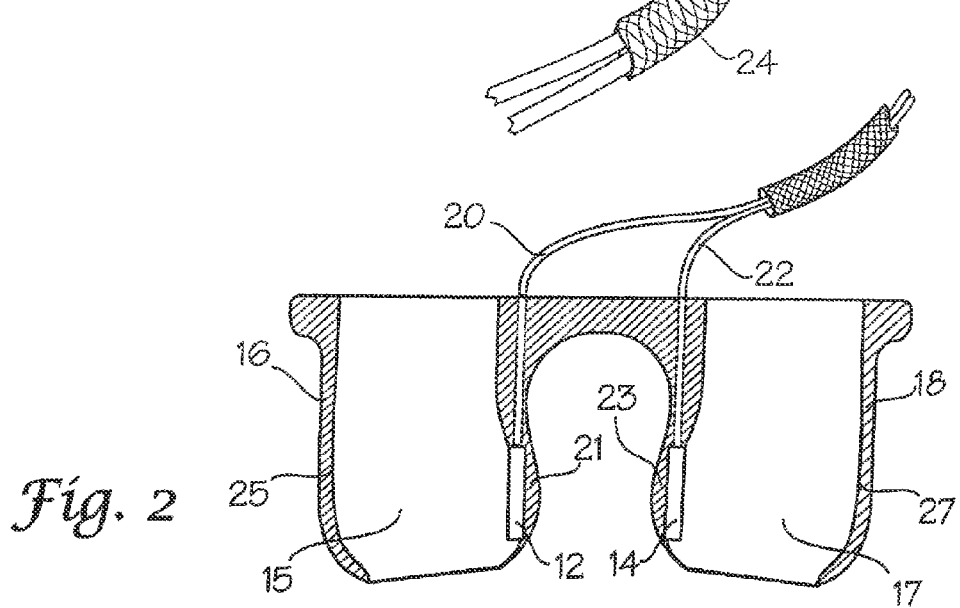
FIG. 2 shows a side cross-sectional view of the embodiment shown in FIG. 1.

FIG. 2 shows a cross-sectional side view of the nasal probe embodiment 10 shown in FIG. 1. The LED(s) 12 and photodetector 14 are positioned across from each other. To monitor oxygen saturation, two or more LEDs are typically required. For plethysmography, only one IR LED is needed. Further, without being limited to any specific mechanism or theory, it is the belief of the inventors that the plethysmogram will show signs of GLOC far earlier than changes in oxygen saturation. However, it is contemplated that the probes and methods of the subject invention may be designed and used to monitor both plethysmography and oxygen saturation of the user.

Insert 16 comprises a medial region 21 and a lateral region 25. Insert 18 also comprises a medial region 23 and a lateral region 27. The user's nasal septum would lie in the space defined by the medial regions 21, 23 of inserts 16, 18, respectively. Accordingly, the medial region represents that portion of the insert that contacts the user's nasal septum. The lateral region represents that portion of the insert that is proximate to the user's nares. Though the disclosed embodiment shows that the inserts completely define an inner channel, with the insert having a medial region and a lateral region, the insert may be fashioned to define less than the full circumference around an inner channel. Wires 20 and 22 are connected to the LED 12 and the photodetector 14, respectively.

FIG. 3 shows a side view of a person having the nasal probe embodiment 10 placed in their nostrils. Wires 20 and 22 are covered and fastened together by a sleeve, which together form wire 32.

FIG. 4 shows a pilot 44 wearing a helmet 46 attached to a mask 40. The mask 40 comprises an air hose 48 attached to the mask compartment 43. The pilot has positioned in his nose 45 the nasal probe 10 shown in FIG. 1. Wire 32 containing wires 20 and 22 passes through hole 42 defined in the mask compartment 43. It will be appreciated by those skilled in the art that the wire may be secured a number of different ways in the mask and/or air hose 48. For example, the hose 48 may have a channel defined therein through which the wire 32 may pass. The embodiment shown in FIG. 4 would most likely comprise fastening the wire 32 to the outside of the hose 48 so that it does not obstruct the actions of the pilot 44. The wire 32 carries the signals from the photodetector to a signal processor and analyzer unit to be discussed in further detail herein. It is important to reiterate that the probe used in conjunction with the mask, nasal, cheek or otherwise, is not limited to the embodiment specifically shown.

Figure 5:
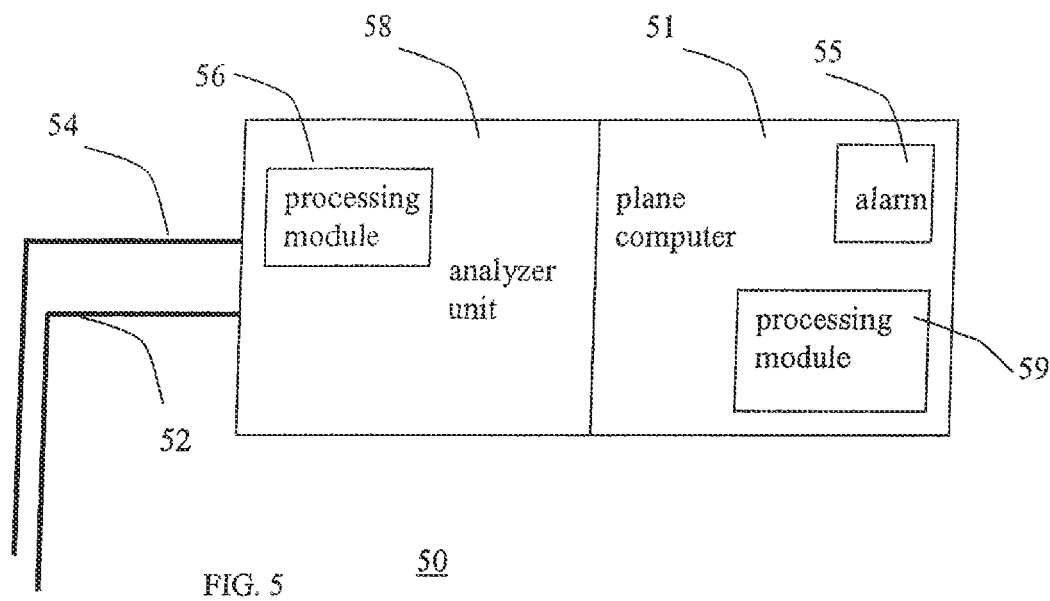
FIG. 5 is a schematic of an embodiment of the subject invention that comprises an analyzer unit integrated with an aircraft computer.

Turning to FIG. 5, there is shown a system 50 for processing signals obtained from a pulse oximeter probe being worn by a pilot and conducting a reaction responsive to certain information received from said pulse oximeter probe. The system comprises an analyzer unit 58 that is configured to receive and process signals from lines 52 and 54. Those skilled in art will appreciate that the signals may be preprocessed to some degree by a separate signal processor and subsequently sent as one signal stream to said analyzer unit 58. Thus, the analyzer unit 58 is configured to receive signals from either lines 52 or 54 or a combination of both. The analyzer unit 58 comprises a processing module 56 comprising software and/or electrical/circuitry components to determine whether the signals received from the pulse oximeter probe correlate to a loss in blood volume indicative of inducing GLOC. The analyzer unit 58 may also comprise a second processing module configured to generate a warning signal.

During a typical high +Gz maneuver, a pilot is trained to take in a maximal deep breath as quickly as possible and to either hold it for a short period of time while bearing down and then performing a rapid forced exhalation, or alternatively, to take in a deep breath and force the air out continuously against pursed lips. With either maneuver, the idea is to "trap" oxygenated blood in the head temporarily (3-5 seconds) and then rapidly allow the blood to return to the lungs. These maneuvers are repeated at 5-10 second intervals throughout the high +Gz period. It is both important to take in a maximal inspiration and then also to bear down and release the breath against resistance. Taking in a deep breath and bearing down forces blood to the head, but if the maneuver is held for too long, venous return to the heart is impeded, flow to the brain decreases and GLOC ensues. Thus, maneuvers to prevent GLOC are a "double edged sword" and must be performed correctly or they can actually exacerbate GLOC.

The disclosed system can be used during centrifuge and aircraft training to provide real time feedback via visual and/or auditory cues to help the pilot optimize these maneuvers. Additionally, when optimal maneuvers are obtained, the system can store the plethysmogram that signals the onset of GLOC. This may be a system that evaluates the amplitude of the pre-+Gz plethysmogram and then recognizes when the plethysmography signals have decreased by a predetermined percentage of the pre-+Gz value which is individualized for each pilot and determines when GLOC is impending (as defined herein a preGLOC condition). Numerous factors including the physical characteristics of the pilot influence their ability to withstand sustained +Gz loads. The individualized information can be loaded into a computer system that continually evaluates the plethysmogram (and therefore blood flow to the head) both during level flight and during +Gz maneuvers and based on predetermined data can determine that the pilot is about to experience forces and declines in blood flow to the head which will result in GLOC if the high +Gz load is maintained. Previous research indicates that unconsciousness ensues approximately 5-8 seconds after cerebral blood flow (CBF) decreases by 72-80% from baseline flow. (Florence G, Bonnier R, Riondet L, Plagnes D, Lagarde D, Van Beers P, Serra A, Etienne X, Tran D. Cerebral cortical blood flow during loss of consciousness induced by gravitational stress in rhesus monkeys. Neurosci Lett. 2001; 305:99-102.) The GLOC warning system could be designed to evaluate the amplitude of the plethysmograph just as +Gz acceleration begins and monitor the amplitude of the plethysmograph during the +Gz maneuver. At a preset percentage of the pre +Gz amplitude an alarm can be actuated. If the pilot does not respond to the alarm and the amplitude continues to drop towards the critical decrease in CBF (e.g., 65-85% below baseline flow) the autopilot could take control and decrease the +Gz load until the plethysmography amplitude increases above a critical level.

Figure 16:
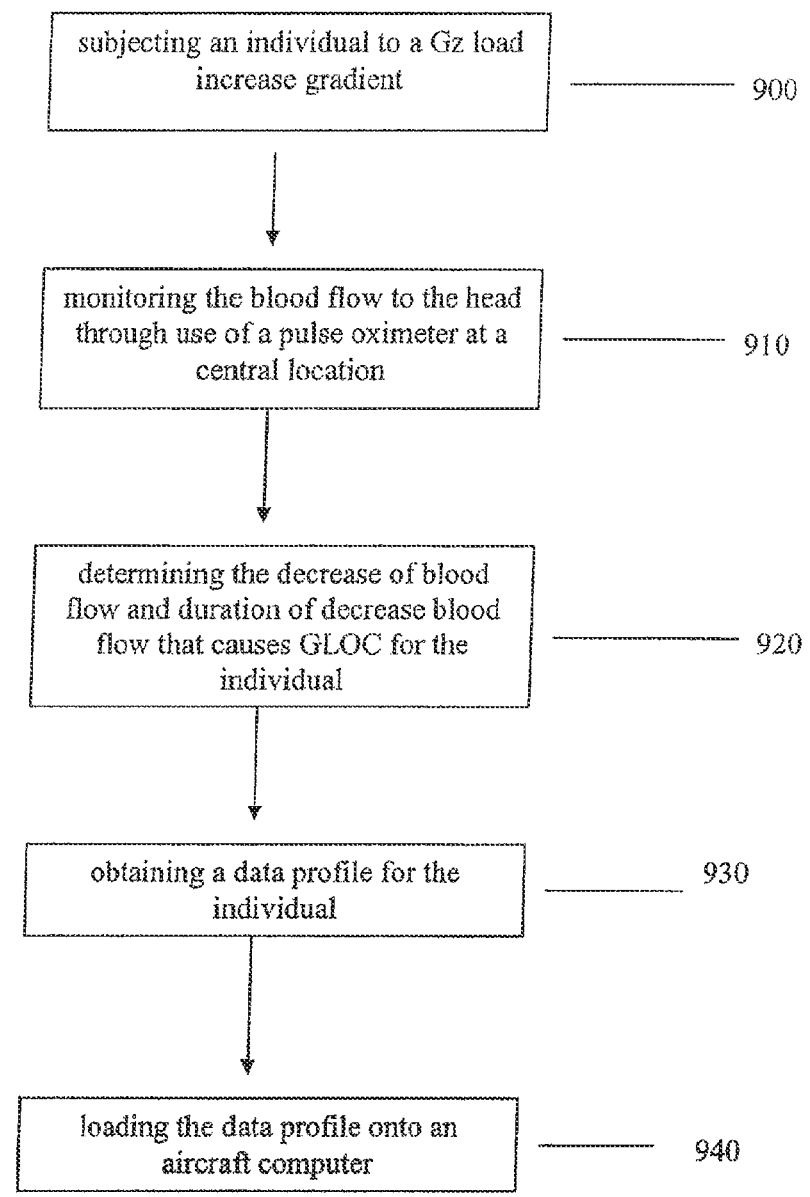
FIG. 16 represents a diagram illustrating a method embodiment of the subject invention for obtaining a personalized data profile for an individual with information for determining whether individual is about to enter GLOC.

Thus, according to another embodiment, as shown in FIG. 16, the subject invention pertains to a method of obtaining an individualized profile concerning the amount of Gz load and duration likely to effect a lowering of head blood flow of an individual to cause GLOC, the method comprising subjecting the individual to a Gz load increase gradient 900, monitoring the blood flow to the head through use of a pulse oximeter at a central location 910; determining the decrease of blood flow and duration of decrease blood flow that causes GLOC for the individual 920; obtaining a data profile for the individual 930; and loading the data profile onto an aircraft computer 940. The implementation of a personalized data profile increases the accuracy of predicting when an individual will undergo GLOC, and can therefore be used to better avert GLOC for the individual. In particular, the processing module containing the data profile can establish a pre-GLOC condition for the individual that when triggered will actuate an alarm and/or direct the aircraft computer to take corrective maneuvers. The terms "pre-GLOC condition" or "condition(s)" represent an empirically determined blood flow and duration conditions preceding GLOC for an individual, and likely to lead to GLOC, but which are established at a predetermined time sufficiently in advance of GLOC so as to allow a pilot to react to avoid GLOC. Use of the personalized profile also will avoid unnecessary false alarms for the individual, which will give the pilot more control over the aircraft, as the physiological conditions sufficient to induce GLOC will vary from pilot to pilot. The pilot can be subjected to Gz loads through use of a centrifuge, air flight maneuvers, or other Gz load producing means. The centrifuge is the most preferred means, as it can be closely controlled and monitored.

In an alternative embodiment, GLOC avoidance training can be implemented using the methods of the subject invention. By closely monitoring the physiological conditions leading up to GLOC for the individual pilot, each pilot can be trained to sense when they are about to enter GLOC and properly react with the valsalva maneuver or other corrective actions. In a preferred embodiment, as part of the training process, the pilot is given a feedback signal to inform the pilot when he is entering a pre-GLOC condition. This will assist in the pilot correlating internal feelings and sensations associated with the pre-GLOC condition in order to more quickly recognize the condition. Furthermore, as is discussed, infra, holding the valsalva maneuver too long can have a counter-productive effect. Utilizing the subject training methods will allow the pilot to practice and refine the optimal valsalva maneuver techniques. Feedback signals may be implemented which will assist the pilot in properly timing the val salva maneuver techniques.

Referring back to FIG. 5, in the system embodiment 50, the analyzer unit 58 is shown as integrated into the aircraft computer 51. The aircraft computer 51 comprises a processing module 59 configured to automatically conduct a corrective flight maneuver with and/or without input from the pilot. The aircraft computer 51 is also connected to an alarm 55 that is actuated upon analyzer unit 58 sending a signal to said aircraft computer 51 indicating a predetermined low-level blood flow. In a specific embodiment the detection and monitoring of changes in blood flow comprises establishing a baseline value of plethysmography signals under normal Gz conditions, and then comparing later obtained plethysmography signals to said baseline value. In a typical embodiment, the analyzer unit comprises a processing module configured to establish the baseline value, continuously monitor the signals and compare to the baseline value.

Figure 6:
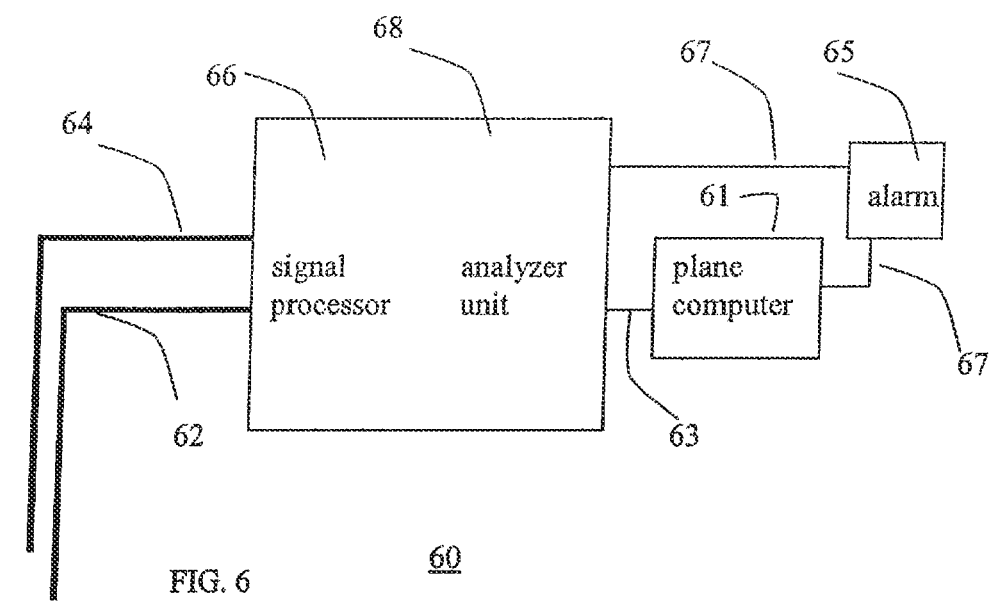
FIG. 6 is a diagram showing a schematic of an embodiment of the subject invention comprising an analyzer unit operationally coupled to an aircraft computer.

FIG. 6 shows an alternative embodiment system 60 for processing signals obtained from a pulse oximeter probe being worn by a pilot and conducting a reaction responsive to certain information received from said pulse oximeter probe. The system 60 comprises an analyzer unit 68 is a stand-alone unit connected to wires 52 and 54. The analyzer unit 68 is connected to an aircraft computer 61 through line 63 and directly to an alarm 65 through line 67. Upon the analyzer unit 68 determining low blood flow, the analyzer unit 68 may actuate an alarm 65 in conjunction with sending the low blood volume signal the aircraft computer 61. For the sake of redundancy, the aircraft computer 61 may also connected to the alarm 65 via wire 69. Like system embodiment 50, the aircraft computer 61 comprises at least one processing module (not shown) configured to conduct a corrective flight maneuver.

The alarm 55 or 65 may be visual and/or audible in nature, such as a light being actuated on the flight panel or a speaker sounding an alarm such as a buzzer. The aircraft computer may also comprise at least one processing module for directing the plane to take corrective flight maneuvers designed to unload the wings of the aircraft so as to decrease the Gz loads on the pilot. One example of such a maneuver includes, but is not limited to, leveling the plane to a steady attitude and altitude decreasing the pitch to level flight attitude. Another example includes immediately leveling the wings while in a steep (60-90 degrees bank angle) high speed turn. The wings' level attitude is designed to induce blood flow to the brain.

The term "aircraft" as used herein refers to any type of craft designed for traveling above the ground. Aircraft is also used in a broader and uncommon sense as to refer to any traveling vehicle that, by the nature of its speed, acceleration and maneuvering, generates force that may induce GLOC in the operator of such aircraft, including vehicles designed for operation on the ground.

The term "wire(s)" as used herein refers to any structure having conductive properties to carry electrical signals. The term wire also is used in an uncommon fashion to denote that the two structures the term wire is used to connect may be substituted by a wireless means of transmitting electrical signals between the two structures. Alternatively, where wires are used to carry signals from the probes to another component, such wires may be substituted with a wireless means of transferring the signals. For example, conventional transmitter/receiver devices could be implemented in the probe and the component to which the probe sends it signals.

The term "communicatingly connected" as used herein refers to any connection either via wires or wireless connection, that is sufficient to convey electrical signals to and/or from at least two components that are communicatingly connected.

As used herein, the terms "signals indicative of blood flow" refers to signals corresponding to blood volume changes in tissue caused by passage of blood, i.e., signals indicative of perfusion or blood flow. See Murray and Foster, The Peripheral Pulse Wave: Information Overlooked, Journal of Clinical Monitoring, 12:365-377 (1996). Typically, these signals are derived from a pulse oximeter probe which produces a waveform produced as a result of absorption of delivered energy (e.g. via a light source) by hemoglobin in red blood cells. Such signals are referred to herein as plethysmography signals.

The term "processing module" may include a single processing device or a plurality of processing devices. Such a processing device may be a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on operational instructions. The processing module may have operationally coupled thereto, or integrated therewith, a memory device. The memory device may be a single memory device or a plurality of memory devices. Such a memory device may be a read-only memory, random access memory, volatile memory, non-volatile memory, static memory, dynamic memory, flash memory, and/or any device that stores digital information.

Figure 7:
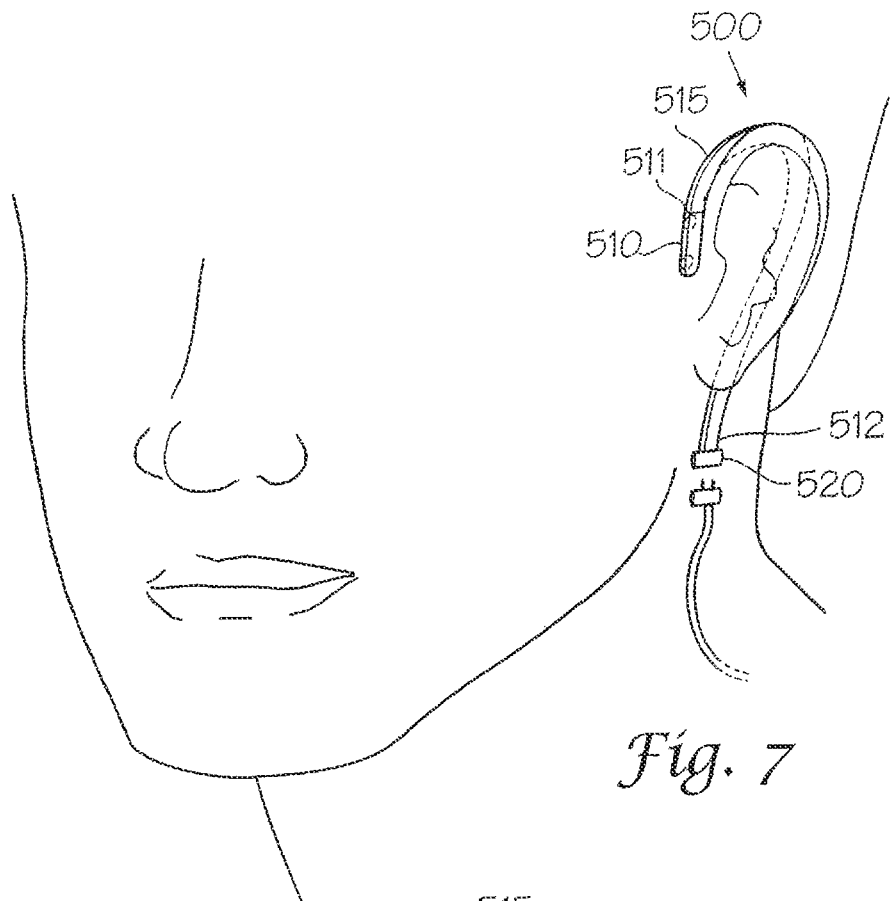
FIG. 7 shows a perspective view of a preauricular reflectance probe embodiment of the subject invention.

Turning to FIG. 7, a pre-auricular reflectance probe 500 is shown. The pre-auricular region is the region in front of the ear. This probe 500 comprises a wiring harness 515 having at its distal end 511 a probe base structure 510 and at its proximal end 512 a connector 520. The pre-auricular reflectance probe embodiment 500 is designed to be secured around the user's ear with the probe base structure 510 typically secured just in front of the tragus of the ear. The probe base structure 510 may be flexible but is preferably rigid or substantially rigid, so as to not bend or deform during use of the probe 500. In a preferred embodiment, the wiring harness is made of a flex circuit such as, but not limited to, those offered by Minco Products, Inc., 7300 Commerce Lane, Minneapolis, Minn. 55432-3177 U.S.A. or NorthPoint Technologies, 207 E. Park Ave., Mundelein, Ill. 60060. The connector 520 may be any suitable connector so as to bring the wires of the wiring harness 515 into electrical communication with a corresponding receptacle with another wire connected to the analyzer unit, or directly onto a receptacle on the analyzer unit.

Figure 8:
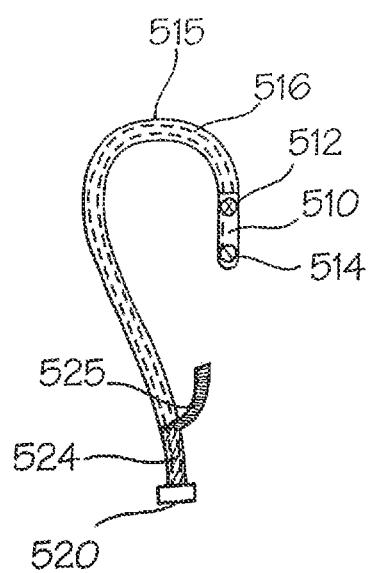
FIG. 8 shows a side view of a pre-auricular reflectance probe embodiment of the subject invention.
Figure 9:
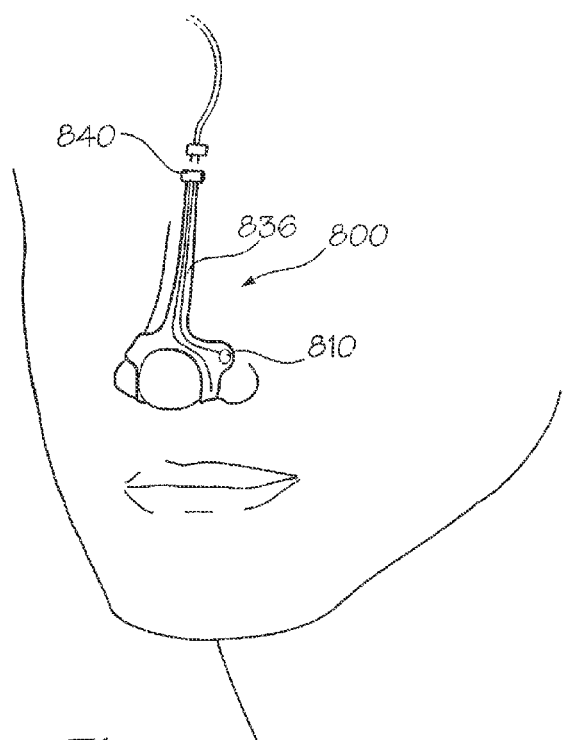
FIG. 9 shows a perspective view of an alar pulse oximeter probe embodiment.
Figure 10:
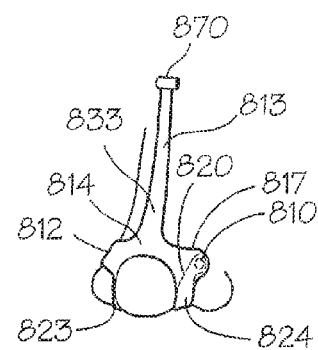
FIG. 10 shows a front perspective view of the alar pulse oximeter probe embodiment shown in FIG. 9.

As shown in FIG. 8, the wiring harness 515 comprise wires 516 made of a conductive substance sufficiently insulated. Wires in the wiring harness 515 are connected to the LED 514 and the photodetector 512 (e.g., a photodiode) of the probe base structure 510. The wiring harness 515 may be provided with an adhesive material 524 that assists with the securement of the probe embodiment in place around the ear and in front of the tragus. Before securing the probe 500 in place, a peel-back layer 525 is removed and the adhesive material 524 adheres the probe to the skin of the user.

The pre-auricular reflectance probe 500 is designed to obtain plethysmography readings and/or oxygen saturation measurements of the temporal artery. The temporal artery is an ideal target since it directly branches off the carotid artery (which is the primary artery to one hemisphere of the brain). The LED 514 directs light to the temporal artery, and depending on the amount of blood flow, or oxygen saturation, the blood in the temporal artery will absorb a quantum of the emitted light. Some of the light is reflected out from the temporal artery and sensed by the photo-detector 512. The amount of light reflected is directly correlated with the amount of blood and/or oxygen saturation of the blood present in the artery. The spacing between the LED 514 and photo detector 512 is critical for obtaining accurate measurements. The space between the LED 514 and photo-detector 512 is typically in the range of about 5 mm to about 35 mm. Preferably, the space is in the range of about 10 mm to about 20 mm. The most preferred range is of the space is about 12 mm to about 16 mm.

In an alternative embodiment, the subject invention is directed to a probe embodiment similar to the pre-auricular reflectance probe, or just the probe base structure with the at least one LED and photo detector, which is embedded into a pilot's helmet, such as in the padding of the helmet. The probe is embedded into the pilot's helmet at a location such that the probe is positioned and stabilized at the preauricular region, upon placement of the helmet on the user's head. Accordingly, in a typical embodiment, the probe is embedded in the padding of a helmet that covers or is proximate to the user's ear.

Figure 11:
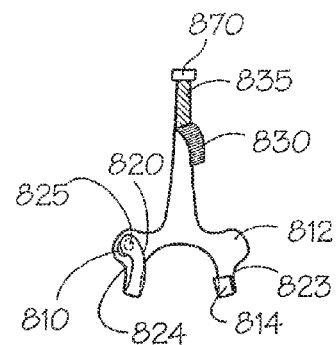
FIG. 11 shows a rear perspective view of the alar pulse oximeter probe embodiment shown in FIG. 9.
Figure 12:
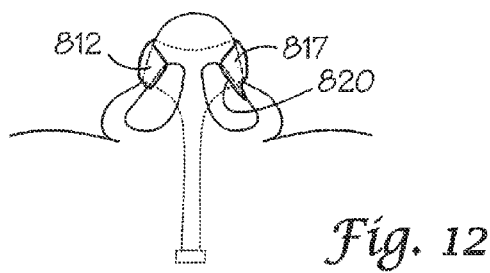
FIG. 12 shows a bottom view of the alar pulse oximeter probe embodiment shown in FIG. 9.

FIGS. 9-12 show a nasal probe embodiment 800 configured for obtaining plethysmography readings and/or oxygen saturation readings from the user's nasal alar region. The nasal probe embodiment 800 comprises a base portion 813 which runs along the longitudinal ridge of the nose. At the distal end 833 of the base portion 813 is a bridge portion 819. The bridge portion 819 runs transversely across the nose and comprises a right flap portion 812 at one end and a left flap portion 817 at its left end. The right and left flap portions 812, 817, respectively, are positioned above the right and left nares of the user. The left flap 817 has attached thereto or integrated therewith at least one LED 810 or other light source. Extending down from the right and left flaps 812, 817 are a right extension 823 and a left extension 824. Attached to or integrated with the left extension 824 is a wing fold 820 that is configured to be inserted into the user's left nostril. The wing fold 820 has at its distal end a photodiode 825 attached thereto or integrated therewith. The wing fold 820 is designed to bend over and be inserted into the user's nostril such that the photodiode 825 is positioned directly across from the LED 810 located on the exterior of the user's' nose. Extension 823 comprises wing fold 814 which is designed to be inserted into the user's right nostril. The positioning of wing fold 814 in the user's right nostril provides a counter force to the wing fold 820 which would tend to pull the probe 800 towards the left. Thus, the right flap 812, right extension 823, and right wing fold 814 act together to assist in securing the nasal probe 800 in place. As shown in FIG. 11, the nasal probe 800 is provided with an adhesive material 835 and a peelback layer 830. Before use, the peel-back layer 830 is removed and the adhesive 835 assists in securing the nasal probe 800 to the skin of the user's nose. At the proximal end 834 of the base 813, a connector 840 is provided. Wires 836 are provided in the nasal probe embodiment and run from the LED 810 and photodiode 825 up to connector 840. Furthermore, a flex circuit as described above may be attached to or integrated with the probe embodiment 800 so as to provide the necessary wiring to the LED 810 and photodiode 825.

Through use of the novel alar probe design described above, the inventors discovered an unexpectedly superior probe position on the lateral side of the nostril just behind the prominent part, which is referred to as the fibro-areolar tissue. The inventors have surmised that this part of the lateral nostril is supplied by the lateral nasal branch of the facial artery, but there are several branches (similar to Kiesselbach's plexus found on the nasal septum). This position also includes the branches of the anterior ethmoidal artery anastamose (lateral nasal branches), which is a branch off the internal carotid. Accordingly, the fibro-areolar tissue site is an unexpectedly optimal site for positioned a probe for use to prevent GLOC. Thus, in a preferred embodiment, the alar probe 800 is dimensioned so that placement onto the fibro-areolar region is optimized for the user.

Figure 17:
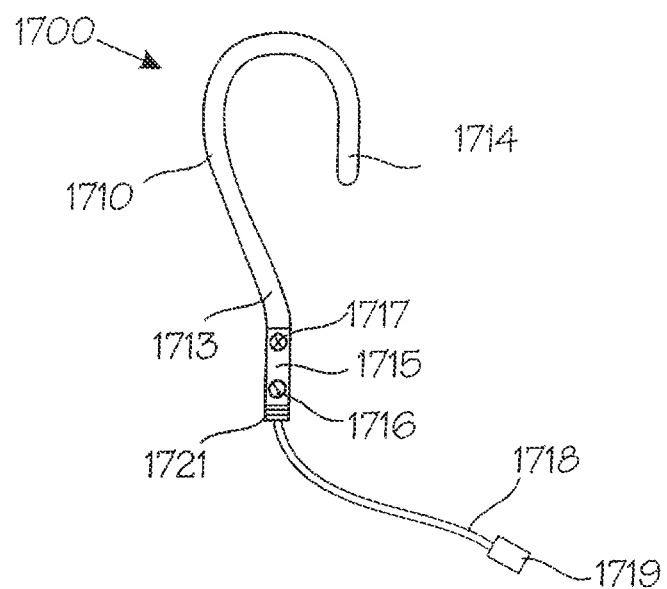
FIG. 17 represents a perspective view of a post-auricular probe embodiment.

According to an additional embodiment, the subject invention pertains to a probe designed for obtaining readings from the post-auricular region. As shown in FIG. 17, the post-auricular region 1711 is the region behind the ear. The posterior auricular artery is a small branch directly off the external carotid. It runs posterior to the auricle and superficial to the mastoid process of the temporal bone. The proximity to the external carotid means that readings from the post-auricular region can provide improved insight to carotid blood flow than a probe on the forehead. Additionally, since collateral flow is not likely at this location it gives a good indication of unilateral flow through the carotid. The other immediate advantage is the superficial nature of the artery coupled with the relative thin layer of skin covering it. The foregoing features, plus the fact that the solid temporal bone is directly below, make the post-auricular region an ideal site for reflectance monitoring.

Another distinct advantage of the reflectance monitoring at the post-auricular region is the lack of venous blood to interfere with saturation readings, as sometimes experienced with forehead models. The thin layer of skin and strong pulsation from the artery allows for correct arterial saturations to be calculated. Other benefits include the lack of hair and fewer sebaceous and sweat glands to interfere with readings. Finally, the area behind the ear is easy to secure a probe to and it is normally out of the way of other devices. Thus, according to another embodiment, the subject invention pertains to a post-auricular reflectance probe 1700 comprising an elongated body portion 1710. The elongated body portion 1710 is curved to wrap around at least a portion of the user's ear. The elongated body portion 1710 comprises a distal end 1713 and a proximal end 1714. At the proximal end 1714, the elongated body has attached thereto or integrated therewith a probe base structure 1715. The probe base structure 1715 comprises at least one LED 1716 and at least one photodetector 1717. The at least one LED 1716 and at least one photodetector 1717 are connected to and in electrical communication with wires 1718. The wires 1718 may extend from the probe base structure 1715 and end in a connector 1719. The wires may be of varied length depending on the application. For example, the wires may end at the proximal end 1721 of the probe base structure 1715, or may run for length out of the probe base structure 1715 and connect to the aircraft computer, or components thereof (e.g. signal processing unit, analyzer unit, etc.).

In an alternative embodiment, the subject invention is directed to a probe embodiment similar to the post-auricular reflectance probe 1700, or just the probe base structure 1715 with the at least one LED and photodetector, which is embedded into a pilot's helmet, such as in the padding of the helmet. The probe is embedded into the pilot's helmet at a location such that the probe is positioned and stabilized at the post-auricular region, upon placement of the helmet on the user's head.

Figure 18:
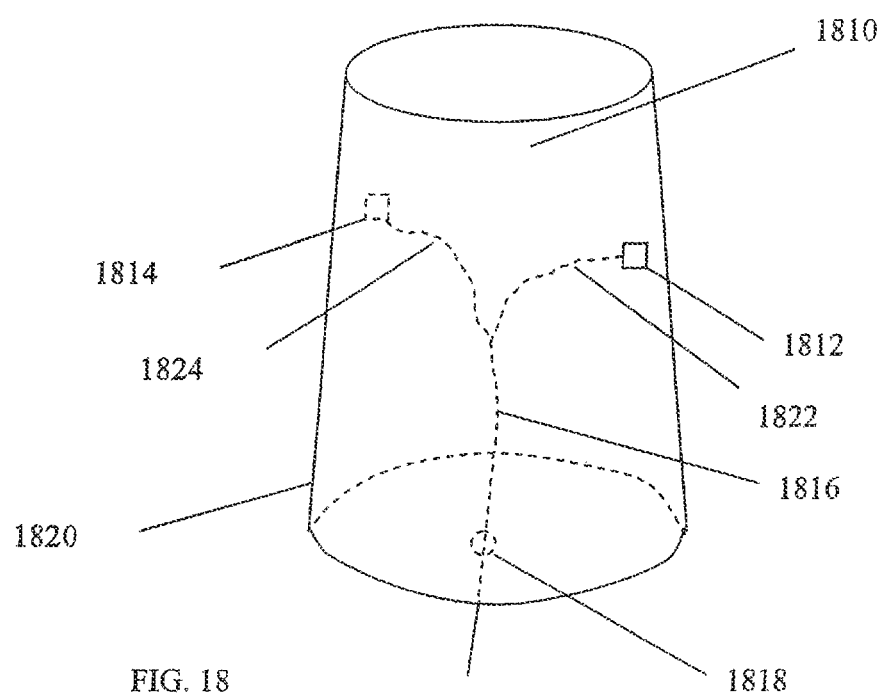
FIG. 18 represents a perspective view of an ear canal probe embodiment for obtaining plethysmography readings from a user's ear canal.

According to an additional embodiment, as shown in FIG. 18, the subject invention pertains to an ear canal probe embodiment 1800 for obtaining plethysmography readings from the ear canal, and more specifically the tympanic artery. The probe 1800 is tapered to assist in placement in the ear, but may alternatively not be tapered. The probe comprises an inner end 1810 which is inserted into the ear canal first, and an outer end 1820. An LED is 1812 is provided on one side of the probe 1800 with a photodetector 1814 provided on the opposite side. Those skilled in the art will appreciate that the spatial arrangement and placement of the LED 1812 and photodetector 1814 may optimized by routine experimentation. Connected to the LED 1812 and photo detector 1814 are wires 1822 and 1824, respectively, which come together to form wire 1816. Wire 1816 exits out the outer end 1820 via exit 1818. The probe 1800 is similar to that described in U.S. Pat. No. 5,213,099, but is specifically tailored and used to obtain plethysmography readings from the ear canal. The '099 patent teaches use of an ear canal probe to obtain oxygen saturation and pulse readings, but does not contemplate or teach use of plethysmography to monitor blood flow and as a method to diminish the risk of GLOC. The inventors have found that plethysmography readings are particularly advantageous in accurately monitoring blood flow (or perfusion), and more accurately and quickly determining pre-GLOC conditions.

Example 1

Figure 13:
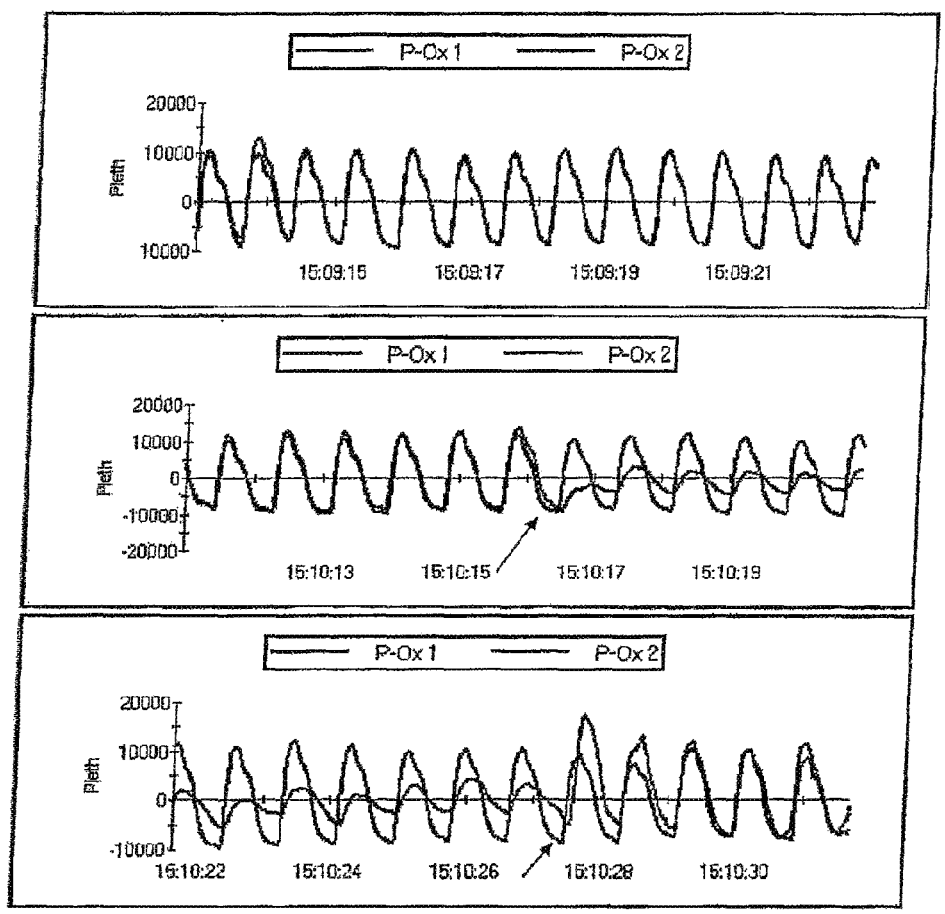
FIG. 13 shows a plethysmograph obtained from the right and left cheek of an individual.

A pulse oximeter probe was positioned on the right cheek and left cheek of an individual. FIG. 13a shows the right and left plethysmograph readings of the individual. At a point in time, the right carotid artery of the individual was depressed thereby stopping blood flow. FIG. 13b shows the effects of pressing on one carotid artery while monitoring from both cheeks. The amplitude of the signal from the right cheek probe dramatically decreases (see arrow). FIG. 13c shows that the when the carotid artery is released, the plethysmography signal from the right cheek spikes (hyperemic response, see arrow) and then returns to normal amplitude. During GLOC, the same or greater decrease in the amplitude of the plethysmograph would be experienced from any probe monitoring from the head. It is believed that the amount of Gz load sufficient to reduce blood flow to the brain, and/or induce GLOC, varies. By knowing what percentage of pre +Gz blood flow leads to GLOC in any individual pilot a personal profile for the pilot may be produced that optimizes the alarm for that individual.

Example 2

The inventors have developed a new processing of the plethysmography signal such that important information may be extrapolated from the signal. This novel processing reveals information not before realized to be obtainable from a plethysmography signal stream. In the past, the plethysmography signal stream was typically obtained from a peripheral site such as the finger, or other extremity. It is the inventors' belief that obtaining the plethysmograph from a central site lacks much of the background noise found in the plethysmograph from a peripheral site, and it is the obtention of this "less noisy" signal that eventually led to the realization that information such as respiration rate and venous capacitance can be extrapolated.

The raw signal stream obtained from a pulse-oximeter probe is related to the amount of light from the LED that hits the photo detector of the pulse-oximeter probe. The magnitude of the signal from the photodetector is inversely proportional to the amount of absorption of the light between the LED and the photodetector (greater absorption results in less light exciting the photodetector). The absorbed light is due to multiple factors, including absorption due to tissue, absorption due to venous blood, absorption due to arterial blood, and absorption due to the pulsation of arterial blood with each heart beat. Typically, the raw signal from the photodetector is processed (e.g. removal of artifacts and autogain of the signal) and also separated into two components. The two components are intended to be the time varying signals that are related to the beat-to-beat variations caused by the pulsation and flow of blood in the arteries (typically called the AC component), and the slowly varying components that is related to the other physiologic and physical properties of the signal, typically called the DC component (including nonpulsatile arterial blood, pulsatile and non-pulsatile venous blood and tissue and bone). The AC signal has been typically called the plethysmography and the DC component overlooked.

The amplitude of the AC component contains information about the amount of arterial blood flowing past the detector. In order to correctly interpret this information, the AC and DC components must be separated more rigorously than in standard monitors. In particular, the pulsatile arterial component should contain only that information that relates to beat-to-beat variations of the heart. The DC component should contain the other, lower frequency effects from physiology such as the respiratory effects, blood pooling, venous impedance, etc.) and physical sensor changes (e.g. changes in the orientation of the probe, etc.).

According to one signal processing method embodiment of the subject invention, the effects of the individual heart beats in the plethysmograph is separated out from the other information, which is fundamentally a slightly different goal than conventional processing, which is basically to obtain an adequate AC component and discarding the DC component. Standard practice is to implement a DC removal technique that involves removing the DC component by a low pass filter. This technique, however, does not sufficiently separate all of the data from the two sources of information. The subject processing method obtains a higher fidelity signal, which is critical when dealing with precise measurements of variables for determining a pre-GLOC condition. In a specific embodiment, the high fidelity AC component and the DC component of the plethysmography signal (previously ignored by those in the art) are achieved by:

1) discretely picking the peaks and troughs of the signal (improved noise/artifact rejection can be achieved by looking for peaks and troughs that exist at the expected heart rate, estimated by Fourier or autocorrelation analysis, or from past good data)

2) finding the midpoints (or minimum values) between peaks and troughs 3) extracting the DC component as the interpolated (and possibly smoothed or splined) line that connects these midpoints (or minimum values)

4) extracting the AC component as the raw signal minus the DC component.

Figure 14:
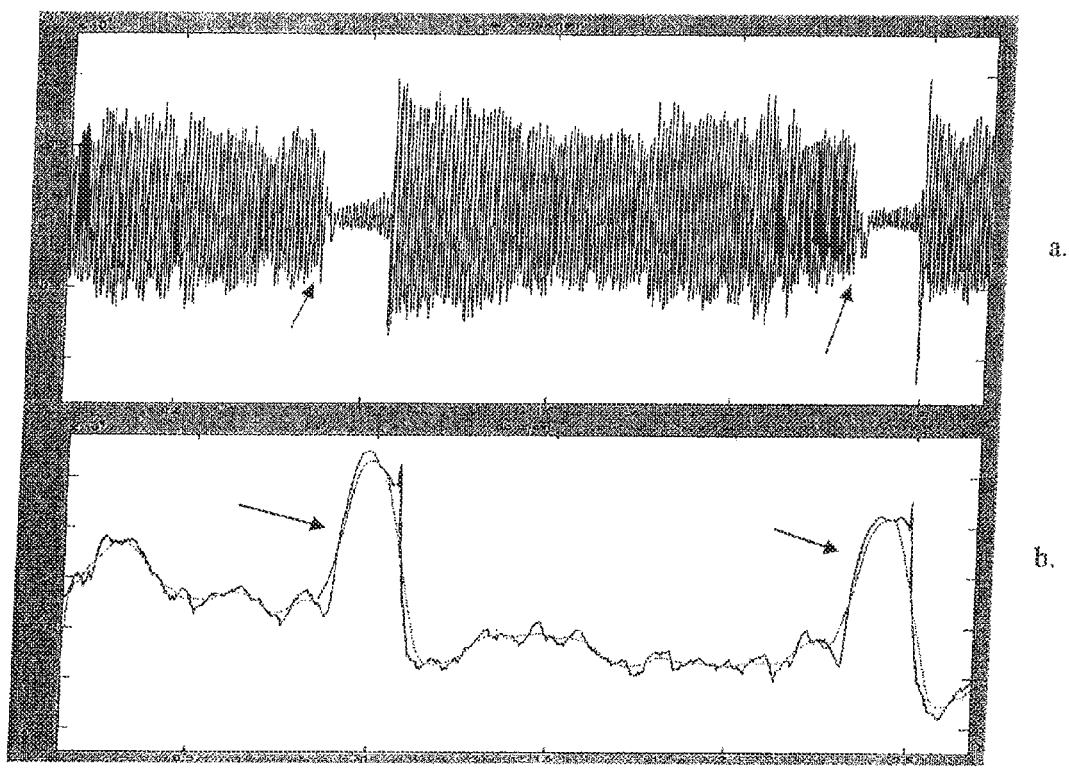
FIG. 14 represents a plethysmograph from a pulse oximeter probe positioned on the cheek. The AC component (or cardiac component for purposes of this example) is provided on the top and the DC offset (or non-cardiac component for purposes of this example) is provided on the bottom. Pressing on the carotid diminishes blood flow, as seen in the AC component (see arrow). Conversely, the DC offset goes up when the carotid is depressed (see arrows).

FIG. 14 represents a plethysmograph from a pulse oximeter probe positioned on the cheek. The AC component is provided on the top and the DC component is provided on the bottom. Pressing on the carotid diminishes blood flow, as seen in the AC component (see arrow). Conversely, the DC component goes up when the carotid is depressed (see arrows). This confirms the inventors' beliefs of the physiological phenomenon that is represented in the DC component. That is, for this example, the DC component increasing demonstrates that there is both less blood flowing to the cheek, and because only the artery in occluded but not venous return there is low venous impedance. The effect is that less blood is flowing to the check, but that blood is able to leave the check. Since there is less blood between the LED and photo detector, there is less absorption of the signal, resulting in a higher DC component signal. By separating the AC and DC components the effects on arterial blood flow and venous return can both be evaluated, a desirable feature when monitoring variables for GLOC.

Example 3

Figure 15:
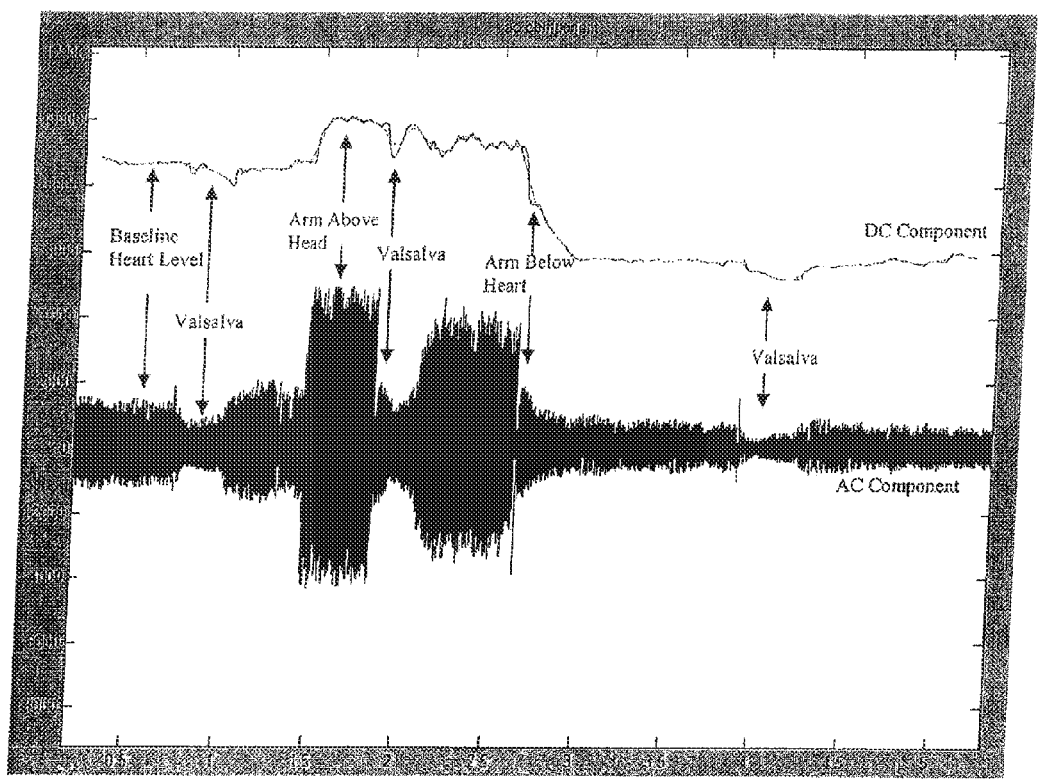
FIG. 15 represents a plethysmograph obtained from the finger. The DC offset is plotted at the top and the AC component at the bottom.

In FIG. 15, the DC component is plotted at the top and the AC component at the bottom. A finger probe was initially placed at heart level and a "baseline" AC component amplitude was obtained. The individual performed a Valsalva maneuver similar to what pilots are taught to do during sustained +Gz in order to prevent GLOC. However, the Valsalva was held for over 10 seconds and this resulted in a decrease in blood flow (reduction in AC component amplitude), a common problem causing GLOC (holding the positive pressure for too long).

Next, the individual placed his finger above the level of his head (while standing up). This results in the amplitude of the AC component increasing. This contradicts convention teaching regarding the AC component, which would predict the exact opposite result and demonstrates the effects of local vessel reactivity to a change in position relative to the heart The AC component increases because there is LESS venous impedance and more blood flow probably due to local vasodilatation in arterioles in the finger between the LED and the detector and there is less venous blood in the finger as demonstrated by the increase in the DC component. The individual again performed a Valsalva maneuver and the blood flow (AC component) decreased and did the DC component due to diminished venous return.

Finally, the individual held his hand below the level of his heart. As the present new understanding of the different components of plethysmography signals would predict, the AC component decreased because of increased venous impedance and a decreased pressure gradient between the arterioles and the venules and the DC component decreased because there was more blood pooled on the venous side between the LED and the photodetector. The same result as above occurred during the Valsalva maneuver. Also note that there is a small, but detectable, decrease in the DC component with each Valsalva. The foregoing further demonstrates that the DC component must be adequately separated in order to obtain a highly accurate AC component signal and to demonstrate effects of the venous side (i.e. venous return).

While various embodiments of the present invention have been shown and described herein, it will be obvious that such embodiments are provided by way of example only. Numerous variations, changes and substitutions may be made without departing from the invention herein. Accordingly, it is intended that the invention be limited only by the spirit and scope of the appended claims. The teachings of all patents and other references cited herein are incorporated herein by reference to the extent they are not inconsistent with the teachings herein.

I claim:

1. A photoplethysmography probe designed for use on a user's nasal alar comprising:
   an elongated base configured for positioning along the user's nasal ridge, the elongated base comprising a proximal end and a distal end;
   a bridge attached to or integral with the proximal end of the elongated base, the bridge having a right end portion and a left end portion;
   a right flap extending from the right end portion of the bridge; a left flap extending from the left end portion of the bridge;
   at least one LED attached to or integrated with either the right flap or the left flap, or both; and
   at least one wing fold extending down from either the right flap or the left flap, or both, the at least one wing fold comprising at least one photodetector attached thereto or integrated therewith,
   wherein if a right wingfold extends from the right flap having an LED attached thereto or integrated therewith, the right wingfold is designed for insertion into the user's right nostril such that a photodetector on the right wingfold is positioned across from the LED attached or integrated with the right flap, and
   wherein if a left wingfold extends from the left flap having an LED attached thereto or integrated therewith, the left wingfold is designed for insertion into the user's left nostril such that a photodetector on the left wingfold is positioned across from the LED attached or integrated with the left flap.

2. The photoplethysmography probe of claim 1, comprising
   a first wing fold extending down from either the right flap or the left flap, the first wing fold comprising at least one photodetector attached thereto or integrated therewith and designed for insertion into the user's right or left nostril; and
   a second wing fold extending down from either the right flap or the left flap, whichever the first flap is not extending down from, and designed for insertion into the user's right or left nostril.

3. The photoplethysmography probe of claim 1, further comprising a connector attached to or integrated with the proximal end of the elongated base, the connector configured for attachment and electrical communication with a corresponding receptacle.

4. The photoplethysmography probe of claim 1, wherein an LED is disposed on both the right flap and the left flap, and the probe comprises a right wing fold extending down from the right flap and a left wing fold extending down from said left flap, wherein both the right wing fold and the left wing fold comprise at least one photodetector attached thereto or integrated therewith.

5. The photoplethysmography probe of claim 1, wherein the at least one wing fold is sufficiently rigid so as to hold its shape upon insertion into the user's nostrils.

6. The photoplethysmography probe of claim 1, wherein a flex circuit may be attached to or integrated with the probe so as to provide wiring to the LED and photodetector.

7. The photoplethysmography probe of claim 1, wherein the probe is configured such that the at least one LED is positioned over the user's nasal alar.

8. The photoplethysmography probe of claim 7, wherein the probe is configured such that the at least one LED is positioned behind the fibro-areolar tissue.

9. A method for obtaining photoplethysmography measurements at the nasal alar, comprising
   securing a photoplethysmography probe onto a user's nasal alar and obtaining photoplethysmography signals,
   wherein the photoplethysmography probe comprises
      an elongated base that is positioned on the user's nasal ridge, the elongated base comprising a proximal end and a distal end;
      a bridge attached to or integral with the proximal end of the elongated base, the bridge having a right end portion and a left end portion;
      a right flap extending from the right end portion of the bridge;
      a left flap extending from the left end portion of the bridge; at least one LED attached to or integrated with either the right flap or the left flap, or both; and
      at least one wing fold extending down from either the right flap or the left flap, or both, the at least one wing fold comprising at least one photodetector attached thereto or integrated therewith,
   wherein if a right wingfold extends from the right flap having an LED attached thereto or integrated therewith, the right wingfold is inserted into the user's right nostril such that a photodetector on the right wingfold is positioned across from the LED attached or integrated with the right flap, and
   wherein if a left wingfold extends from the left flap having an LED attached thereto or integrated therewith, the left wingfold is inserted into the user's left nostril such that a photodetector on the left wingfold is positioned across from the LED attached or integrated with the left flap.

10. The method of claim 9, wherein the photoplethysmography probe comprises a first wing fold extending down from either the right flap or the left flap, the first wing fold comprising at least one photodetector attached thereto or integrated therewith and inserted into the user's right or left nostril; and a second wing fold extending down from either the right flap or the left flap, whichever the first flap is not extending down from, and inserted into the user's right or left nostril.

11. The method of claim 9, further comprising a connector attached to or integrated with the proximal end of the elongated base, the connector being in electrical communication with a corresponding receptacle.

12. The method of claim 9, wherein an LED is disposed on both the right flap and the left flap, and the probe comprises a right wing fold extending down from the right flap and a left wing fold extending down from said left flap, wherein both the right wing fold and the left wing fold comprise at least one photodetector attached thereto or integrated therewith.

13. The method of claim 9, wherein the at least one wing fold is sufficiently rigid so as to hold its shape while in the user's nostrils.

14. The method of claim 9, wherein a flex circuit may be attached to or integrated with the probe so as to provide wiring to the LED and photodetector.

15. The method of claim 9, wherein the at least one LED is positioned over the user's nasal alar.

16. The method of claim 15, wherein the at least one LED is positioned behind the fibro-areolar tissue.

* * * * *